United States Patent [19]

Daughdrill

[11] Patent Number: 5,007,122

[45] Date of Patent: Apr. 16, 1991

[54] HEAD RESTRAINT

[76] Inventor: Annette S. Daughdrill, 13228 Briargrove Ave., Baton Rouge, La. 70810

[21] Appl. No.: 563,049

[22] Filed: Aug. 6, 1990

[51] Int. Cl.⁵ .................................................. A47G 9/00
[52] U.S. Cl. .......................................... 5/434; 5/436; 269/328
[58] Field of Search ............... 5/434, 436, 437, 443, 5/444; 269/328; 128/202.18

[56] References Cited

U.S. PATENT DOCUMENTS

| | | | |
|---|---|---|---|
| 3,347,544 | 10/1967 | Uffenorde | 5/434 |
| 3,482,571 | 12/1969 | Behrendt | 5/436 |
| 3,938,205 | 2/1976 | Spann | 5/431 |
| 3,957,262 | 5/1976 | McReynolds | 5/437 |
| 4,058,112 | 11/1977 | Johnson | 269/328 |
| 4,135,504 | 1/1979 | Spann | 5/444 |
| 4,453,540 | 6/1984 | Frain | 269/328 |
| 4,612,678 | 9/1986 | Fitsch | 5/82 R |
| 4,688,780 | 8/1987 | Hanz | 269/328 |
| 4,752,064 | 6/1988 | Voss | 269/328 |
| 4,757,983 | 7/1988 | Ray et al. | 269/328 |
| 4,805,603 | 2/1989 | Cumberland | 5/436 |

*Primary Examiner*—Alexander Grosz
*Attorney, Agent, or Firm*—Robert C. Tucker; William David Kiesel

[57] ABSTRACT

A head restraint is provided, comprising a resilient block having an exterior surface and including a bottom; an inclined front face having a top edge; a rear face; sidewalls; a cavity in the front face forming an interior cavity wall, the intersection of the cavity and the front face having a circumference less than the rear peripheral circumference of the head of a patient; and a split, opening between the cavity and the exterior, intersecting the rear face, the top edge and the front face above the cavity.

6 Claims, 3 Drawing Sheets

HEAD RESTRAINT

BACKGROUND OF THE INVENTION

1. Field of the Invention

This invention relates generally to devices which are used to immobilize medical patients and, more particularly, to devices which are used to immobilize the head of a patient.

2. Prior Art

In the medical field there are many different devices used to immobilize various body parts in order to further the particular medical treatment being applied to a patient. When a patient is intubated through the mouth or nose, it is desirable that the patient's head remain immobilized in order to prevent accidental extubation. This is especially true with children, who have shorter airways than adults such that even slight slippage of an endotracheal tube may result in extubation. Copious secretions often loosen tape or other prior art securing devices and the weight of the ventilator tubing itself can pull the tubing out of place. When the variable of a fighting child is added, even with the child's arms restrained, a very difficult situation exists. Medication can be used to sedate or paralyze the patient However, it then becomes difficult to assess any neurological changes that may be occurring. Intubating a child is a difficult procedure. Reintubating a child is even more difficult because the trachea usually has been traumatized from the initial intubation and resulting in tracheal edema. In cases where the intubation is for surgical reasons, such as in craniofacial surgery or for a cricoid split, it may be impossible to reintubate.

Prior art methods of head immobilization include placement of sandbags on each side of the head, which is both uncomfortable and ineffective. A device is needed which can be easily installed and removed, is relatively comfortable for the patient during long term usage (days to weeks in an intensive care setting), and which immobilizes the head of the patient.

SUMMARY OF THE INVENTION

Therefore, it is an object of this invention to provide a head restraint which immobilizes the head of a patient and which can be easily installed and removed.

It is a further object of this invention to provide a head restraint which aids in preventing accidental extubation of tubing from a patient's mouth or nose.

It is another object of this invention to provide a head restraint which holds the patient's head in a natural and comfortable position.

It is still another object of this invention to provide a head restraint which accomplishes the above objects and is relatively inexpensive to produce.

It is yet another object of this invention to provide a head restraint which is disposable.

Accordingly, a head restraint is provided, comprising a resilient block having an exterior surface and including a bottom; an inclined front face having a top edge; a rear face; sidewalls; a cavity in the front face forming an interior cavity wall, the intersection of the cavity and the front face having a circumference less than the rear peripheral circumference of the head of a patient; and a split, opening between the cavity and the exterior, intersecting the rear face, the top edge and the front face above the cavity.

The block may be further provided with a back support tongue and/or side extensions for tilted orientation of the block.

DETAILED DESCRIPTION OF PREFERRED EMBODIMENTS OF THE INVENTION

Figure 1:
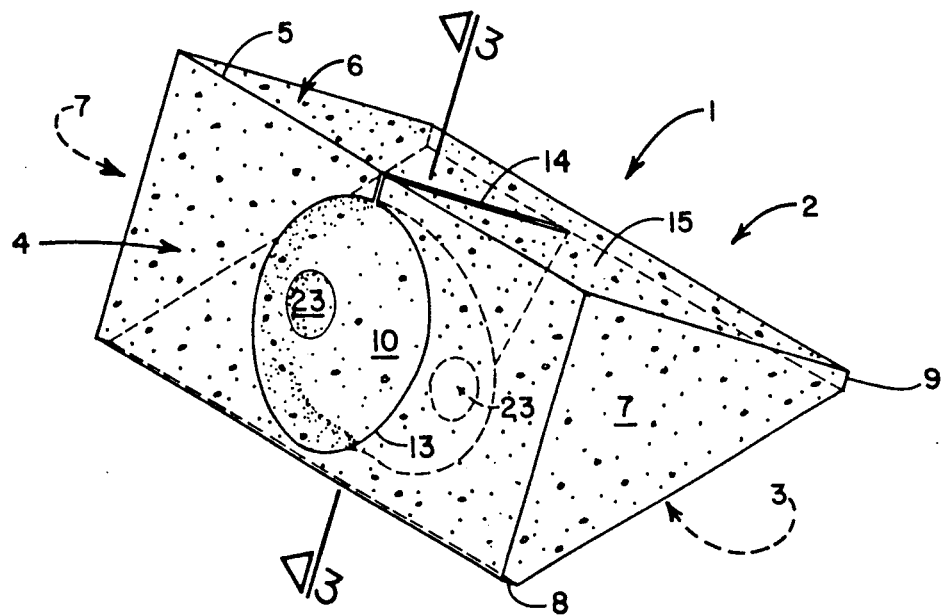
FIG. 1 is a front perspective view of an embodiment of the invention.
Figure 2:
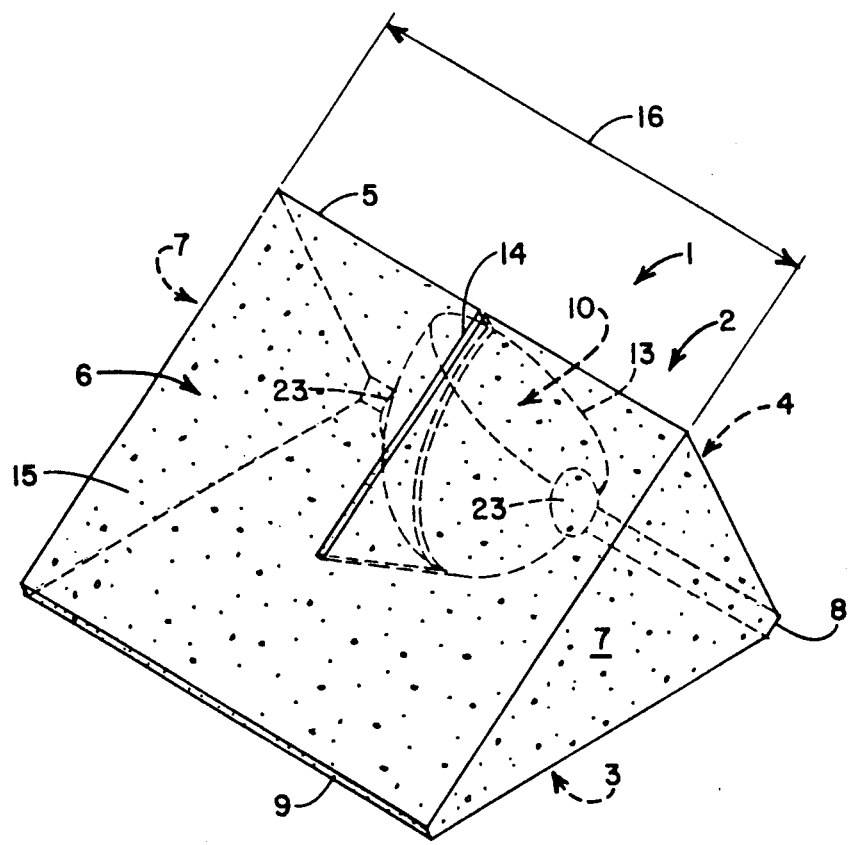
FIG. 2 is a rear perspective view of the embodiment shown in FIG. 1.
Figure 3:
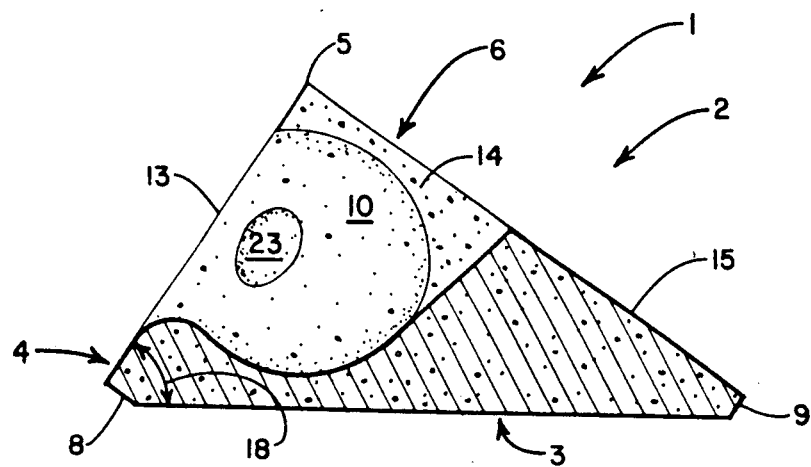
FIG. 3 is a sectional view taken along view line 3—3 of FIG. 1.

As shown in FIGS. 1-4, the invention 1 generally comprises a resilient block 2, preferably constructed of pliable foam rubber or other suitable material. Block 2 has a bottom 3, an inclined front face 4 having top edge 5, a rear face 6 and sidewalls 7. Front chamfer 8 and rear chamfer 9 may be included to eliminate sharp and thin angular edges which may tear easily. A cavity 10 is formed in front face 4 to receive the rear side 11 of a patient's head 12.

Figure 4:
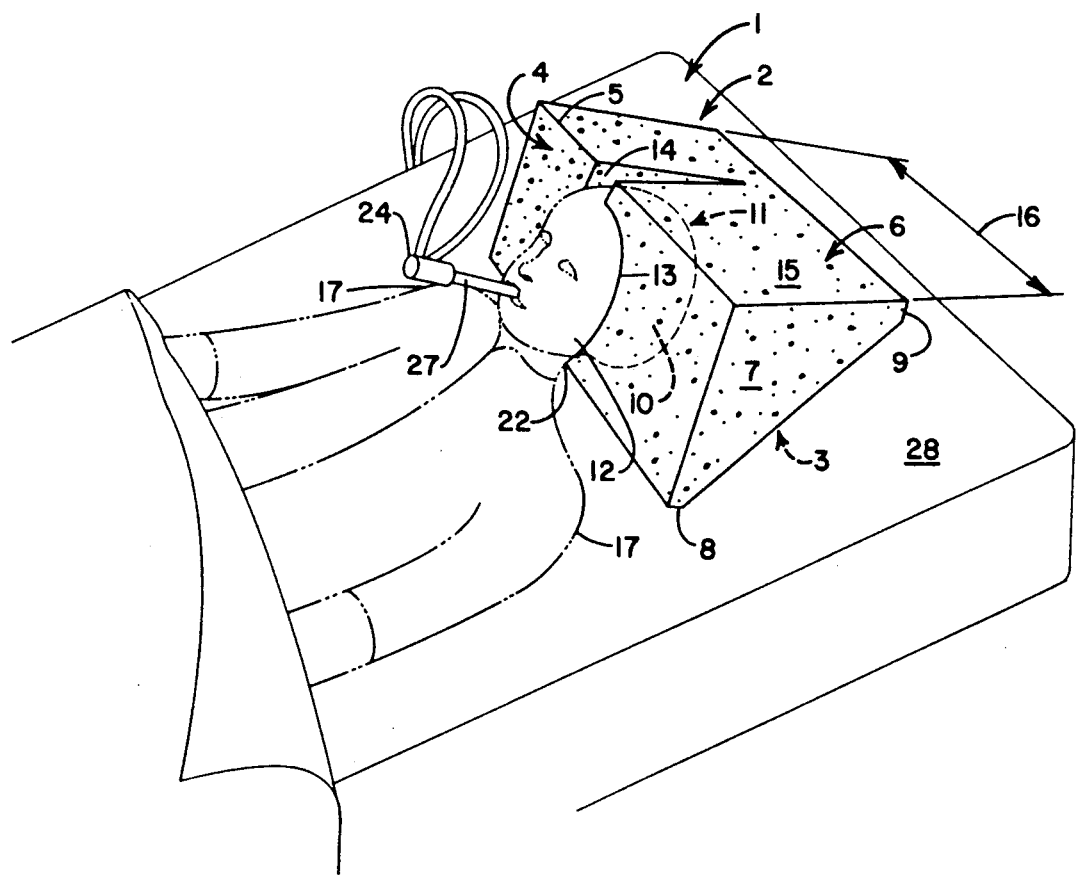
FIG. 4 is a front perspective view of the embodiment shown in FIG. 1 in place on a patient.

The intersection 13 of cavity 10 and front face 4 is generally oval-shaped, and should have a circumference less than the rear peripheral circumference of a patient's head 12. For the purposes of this description, "rear peripheral circumference" is the circumferential measurement around the patient's head 12 at the point where it exits cavity 10, when the invention 1 is installed. As shown in FIG. 4, the rear peripheral circumference would be measured where intersection 13 meets the patient's head, and may include the upper portion of the patient's neck 22. Cavity 10 should substantially follow the rear peripheral contour of the patient's head 12. The term "rear peripheral contour" describes the shape of the rear side 11 of the patient's head 12 which is contained within cavity 10. Preferably, cavity 10 is slightly smaller than the rear peripheral contour of the patient's head 12 to insure a snug fit.

Since the circumference of intersection 13 is smaller than the peripheral circumference of the patient's head 12, and since cavity 10 is preferably slightly smaller than the peripheral contour of head 12, a split 14 is provided to allow the block 2 to be installed or removed. Split 14 opens between cavity 10 and the exterior surface 15 of block 2, intersecting rear face 6, top edge 5 and front face 4 above cavity 10, as shown.

As best seen in FIG. 4, cavity 10 is dimensioned to contact a substantial portion of the top, rear and sides of a patient's head, while leaving the face of the patient exposed.

As shown in FIG. 4, installation is simple. Split 14 is spread apart, allowing the patient's head 12 to be placed in cavity 10. When the weight of patient's head 12 rests in cavity 10, split 14 closes and cavity 10 is slightly compressed against head 12, holding it in position, helping to prevent extubation of endotracheal tubing 27, connected to ventilator tubing 24. Split 14 may remain slightly expanded, depending upon the size of head 12. Preferably ear cavities 23 are provided, alignable with the patient's ears, in order to prevent pressure on the ears. It is preferable that the width 16 of block 2 extend approximately to or past the patient's shoulders 17 for additional stability. Thus, the head 12 is held in position while being resiliently supported for comfort.

Figure 5:
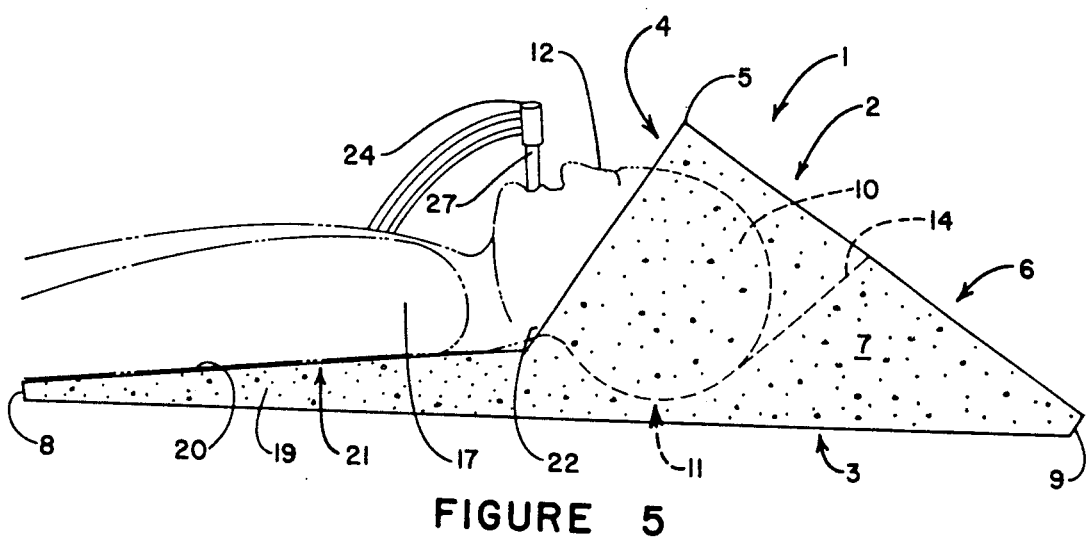
FIG. 5 is a side view of an alternate embodiment of the invention in place on a patient.
Figure 6:
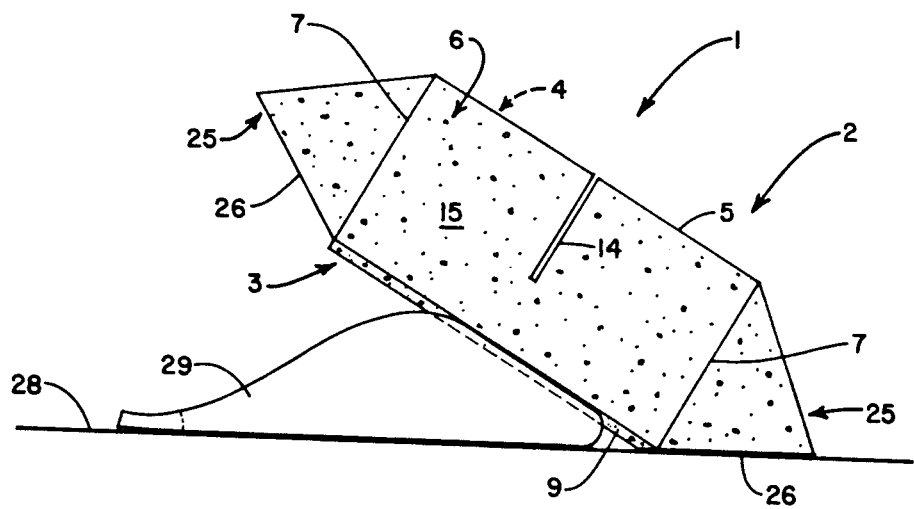
FIG. 6 is a rear view of an alternate embodiment of the invention.

As can be seen, the inclination angle 18 of front face 4, together with the shape and depth of cavity 10, determine the orientation of the patient's head 12. It is preferred that angle 18 and the shape and depth of cavity 10 be such that head 12 is in a normal position, as if standing upright, in order to establish maximum comfort. In some instances, it may be desirable to utilize the embodiment shown in FIG. 5, in which a back support tongue 19 extends from front face 4 and bottom 3 for the full width 16 of block 2. Tongue 19 has a slightly inclined top surface 20, which supports and raises the back 21 of the patient, allowing the rear side 11 of head 12 to be received in cavity 10 at a point slightly below the level of back 21 in order to create a more normal posture. One or more side extensions 25, extending from sidewalls 7 as shown in FIG. 6, may be provided to allow the patient's head 12 and body to be turned together (i.e. "log-rolled") by placing an object such as a wedge or pillows 29 under the patient's body and under bottom 3 of block 2. In this situation, the inclined bottom surface 26 of side extension 25 provides additional support against the bed surface 28.

It has been found that one size of block 2 will accommodate a wide range of head sizes, so long as the peripheral circumferences are larger than the circumference of intersection 13. However, it may prove to be desirable to stock several sizes of restraints 1 for maximum comfort and utility. It may also prove to be useful to stock restraints 1 wherein the inclination angles 18 and the shapes and depths of cavities 10 are varied. These and other alternate embodiments of the invention 1 will occur to those skilled in the art, and are intended to be included within the scope and spirit of the following claims.

I claim:

1. A head restraint adapted to immobilize the head of a patient in a supine position, comprising a resilient block having an exterior surface and including:
   a. a bottom;
   b. an inclined front face having a top edge;
   c. a rear face;
   d. sidewalls;
   e. a cavity in said front face forming an interior cavity wall dimensioned to contact a substantial portion of the top, rear and sides of a patient's head, while leaving the face of the patient exposed, the intersection of said cavity and said front face having a circumference less than the rear peripheral circumference of the head of a patient; and
   f. a split, opening between said cavity and said exterior surface, intersecting said rear face, said top edge and said front face above said cavity.

2. A head restraint according to claim 1, wherein the shape of said cavity substantially follows the rear peripheral contour of a patient's head.

3. A head restraint according to claim 2, wherein said cavity is slightly smaller than the rear peripheral contour of a patient's head.

4. A head restraint according to claim 3, wherein two ear cavities are provided in said interior cavity wall, alignable with a patient's ears.

5. A head restraint according to claim 1, wherein said block further includes:
   g. a back support tongue extending from said front face and said bottom, said tongue having a top surface intersecting said front face just below said cavity.

6. A head restraint according to claim 1, wherein said block further includes at least one side extension extending outward from one said sidewall above said bottom.

* * * * *